United States Patent [19]

Lemaster et al.

[11] Patent Number: 4,831,880
[45] Date of Patent: May 23, 1989

[54] METHOD AND APPARATUS FOR DETERMINING VERTICAL DENSITY PROFILES IN WOOD COMPOSITES, USING ACOUSTIC EMISSION

[75] Inventors: Richard L. Lemaster, Pinole; David A. Dornfeld, Berkeley, both of Calif.

[73] Assignee: The Regents of the University of California, Berkeley, Calif.

[21] Appl. No.: 229,822

[22] Filed: Aug. 8, 1988

[51] Int. Cl.[4] ............................................ G01N 29/00
[52] U.S. Cl. ...................................................... 73/587
[58] Field of Search ................. 73/573, 587, 801, 32 A

[56] References Cited

U.S. PATENT DOCUMENTS

| | | | |
|---|---|---|---|
| 2,790,968 | 4/1957 | Cook et al. | 73/573 |
| 3,066,525 | 12/1962 | Harris | 73/629 |
| 3,209,177 | 9/1965 | Minasian | 73/644 |
| 3,986,391 | 10/1976 | Vahaviolos | 73/801 |
| 4,309,903 | 1/1982 | Ono | 73/587 |

*Primary Examiner*—Michael J. Tokar
*Assistant Examiner*—Lawrence G. Fess
*Attorney, Agent, or Firm*—Owen, Wickersham & Erickson

[57] ABSTRACT

Method and apparatus for determining vertical density profiles in wood composites. A fly cutter is rotated across the edge of a wood composite panel to produce acoustic emissions that themselves produce an RMS voltage. The changes is RMS voltage so produced are recorded and thereby the acoustic emission is recorded. The detected signal is transformed into electrical signals, amplified and transmitted to a suitable detecting transducer.

12 Claims, 5 Drawing Sheets

METHOD AND APPARATUS FOR DETERMINING VERTICAL DENSITY PROFILES IN WOOD COMPOSITES, USING ACOUSTIC EMISSION

This invention relates to method and apparatus determining vertical density profiles in wood composites, doing so by using acoustic emission.

BACKGROUND OF THE INVENTION

The manufacturing of wood composite board and building materials requires the evaluation of many variables. The sizes of the wood fibers and particles, the glue content, the pressure, the pressing time, the temperature, and other factors must be determined and checked in order to produce a board of consistent quality. An accepted measure of consistency is the density profile of the board. If the density profile of a composite board with the desired strength characteristics can be reproduce,, then the strength characteristics can be maintained.

Several different methods for evaluating density profiles have been used in industry and in the laboratory. The gravimetric method is the direct method; the density measurements, in this case, can be evaluated approximately every 0.076 cm (0.030 in.) of thickness.

Two methods involving radiation sources have also have been evaluated. Parker et al. (1980) used X-rays to produce a photographic image of the profile of a composite wood specimen. This method allows for virtually continuous density measurements across the cross-section of the board, with correlations made with known standards. Laufenberg (1985) and Winistorfer et al. (1986) used a gamma ray source to scan the thickness of a specimen. The transmitted radiation was then correlated to the material density, and a continuous measurement was again possible.

Of the methods discussed, the conventional gravimetric method for density determination is the most time-consuming and is the least resolute. Although the density calculations are the most direct (weight/volume), as the specimen is planed the measurements become more difficult to obtain, due to the decreasing thickness. A thicker specimen would be easier to handle, but would also require more time, due to the greater number of sections to be removed.

The x-ray and gamma ray techniques for density measurements each provide continuous profiles of the specimen, but they also require radiation sources and a greater knowledge of equipment operation by the user. The radiation methods are faster than the gravimetric method and provide information about densities at specific points rather than averages over small sections. Both methods are claimed to be nondestructive; however, this would not be the case in practical applications in industry. The samples being evaluated must be no more than 7.62 cm (3 in.) in width; so some part of the manufactured board must be cut. The operation of these densitometers would not only require training, but would also incur a substantial initial cost before consistent measurements could be made.

We have now found that acoustic emission (AE) can be used to evaluate the density profile of a wood composite.

SUMMARY OF THE INVENTION

The present method moves a rotating fly cutter or similar tool across the edge of a wood composite panel, while an AE transducer mounted on the panel, records the changes in the RMS voltage. This technique, while destructive, can be considered a non-destructive technique in the practical sense, due to the fact that only a small 2.54 cm (1 in.) wide by 0.25 cm (0.1 in.) thick notch is made in the panel and hence this shallow notch does not affect the final product.

ACOUSTIC EMISSION

Figure 1:
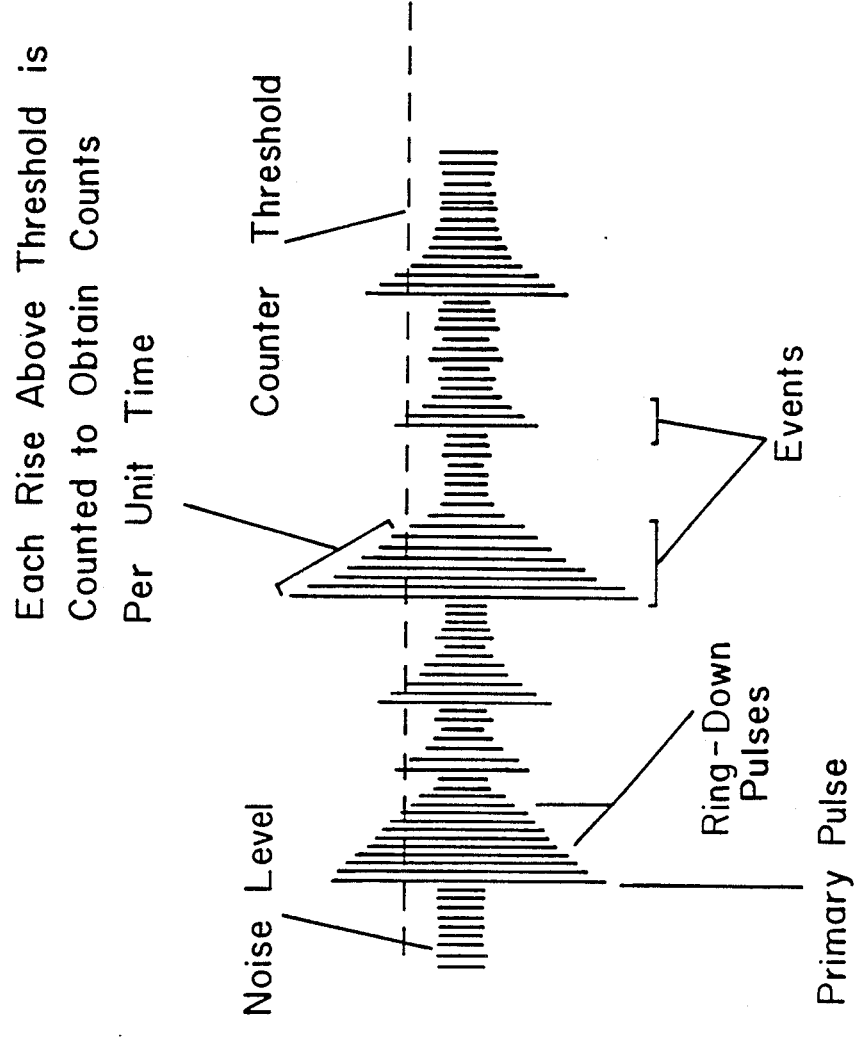
FIG. 1 is a schematic diagram of a typical acoustic emission signal.

Acoustic emission can be defined as the stress of pressure waves generated during dynamic processes in materials (see FIG. 1). Though usually in the ultrasonic range (typically 100 kHz to 1 MHz), these waves can sometimes be sensed by the unaided ear, as when timber cracks upon being loaded to a value near failure.

The AE signal is usually detected by an instrumentation system that uses sensors (transducers) which, when stimulated by stress waves, transform mechanical excitations into electrical signals. These electrical signals are then amplified and transmitted to an oscilloscope, counter, root mean square (RMS) voltmeter, recorder, or spectrum analyzer, depending on the type of analysis. The most common type of transducer is a piezoelectric ceramic element, for example, of lead zirconate titante.

A significant problem in the application of AE in process control is the analysis of interpretation of the signals. An actual AE signal is non-periodic, contains many frequencies, and cannot be described by an explicit mathematical relationship. Therefore statistical tools are used in analyzing AE data. Among the various methods frequently used to characterize the emission from a material are: the cumulative count, count rate, RMS voltages, spectral analysis, probability density function, auto-correlation function, and amplitude distribution analysis The voltage, V, of the signal can be theoretically represented as an exponentially damped sinusoidal wave according to the relationship:

$$V = V_o e^{-\beta t} \cos 2\pi f\, t \qquad [1]$$

where
  $V_o$ = the threshold voltage
  V = the initial output voltage of the transducer
  $\beta$ = the damping factor
  f = the linear frequency
  t = time in seconds.

The AE signal is due to an AE event, which is defined as a single occurrence of AE activity, and is illustrated in FIG. 1. A sharp tap on a transducer will register one event, while a vigorous shake will register several events The number of counts resulting from the events is the number of times the signal caused by the events exceeded a preset threshold voltage and depends on the energy contained in the event and the damping factor $\beta$. It can be assumed that the output voltage of a transducer is proportional to the square root of the energy released during a given deformation process. This is true because the output voltage of a piezoelectric disk is proportional to the stress on the disk face and because the energy density of an elastic stress wave is proportional to the square of the stress.

The RMS voltage of a continuous AE signal can be used to measure the energy of the AE signal. Here, the term "continuous emission" (as defined by the 1974 U.S. Acoustic Emission Working Group, refers to a sustained signal level whose characteristics are such that ". . . the average time interval between the beginning of the emission signals of comparable amplitude is less than or comparable to the duration of the emission signals". The RMS value of the AE signal is that value of a DC signal which, if passed through the same circuit for the same times, would produce the same expenditure of energy as the AE signal. Analytically, it is defined as:

$$RMS = \left[ \frac{1}{\Delta T} \int_0^{\Delta T} V^2(t) dt \right]^{\frac{1}{2}} \quad [2]$$

where
 $V(t)$=the function of the signal with respect to time.
 $\Delta T$=the time period.

In previous studies, it has been determined that the acoustic emission is generated at the primary deformation zone at the tip of a cutting tool moving through wood. Furthermore the levels of acoustic emission generated where found to be sensitive of AE to density gave rise to the idea of correlating AE levels to density profiles in composite wood.

Figure 2:
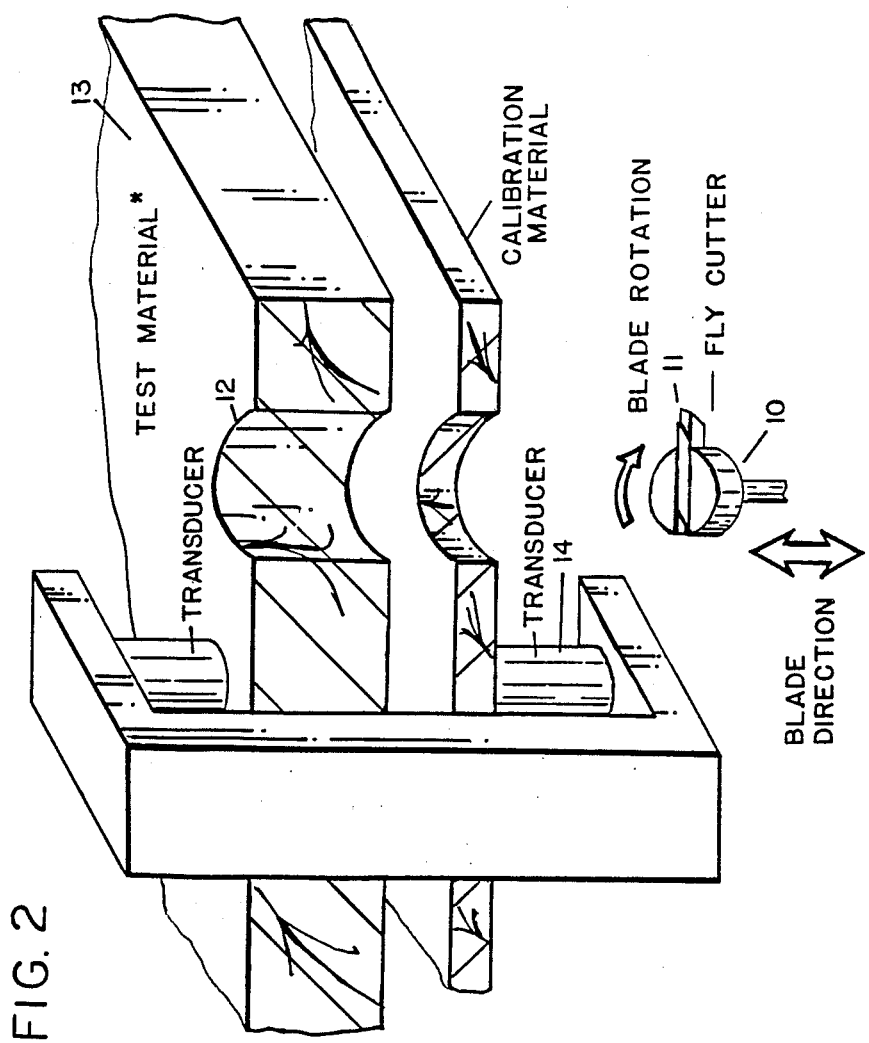
FIG. 2 is a perspective view of a set up with apparatus, test material, and calibration material exemplifying apparatus that performs the method of the invention.
Figure 3:
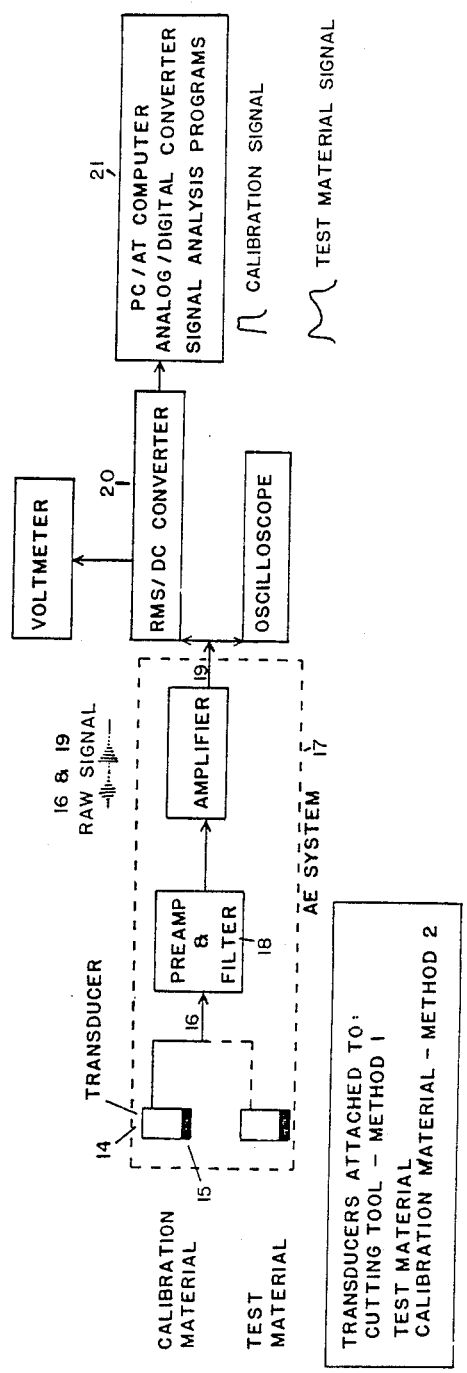
FIG. 3 is a schematic illustration of the amplifying, detecting, and measurement apparatus employed with the set up of FIG. 2.

The present invention was devised in an effort to provide a non-destructive testing technique. As shown in FIG. 2, the blade is rotated, while the specimen is held stationary. This makes possible the testing o full-sized panels, and consequently an on-line testing procedure is feasible. The need for the calibration material to be tested every time can be eliminated by the use of wear-resistant cutting tools of carbide or diamond-coated tools. This simplifies the testing procedure but should be weighed against the higher cost of the cutting tools.

A fly cutter 10 with a carbide single point cutter 11 maybe used. A cutting arc of 4.44 cm (1.75 in.) rotating at 1200 rpm may be used to remove a maximum of 0.25 cm (0.1 in.) from the edge 12 of a wood composite specimen 13. Preliminary work showed that the feed speed selected was critical in obtaining a good density profile. Faster feed speeds may be used, but a feed of at least 1.9 cm/min (0.75 in/min) is recommended. An AET 175 kHz transducer 14 may be attached to the specimen 13, e.g., 2.54 cm (1 in.) from the mid-point of the cutter 11, using a 4 pound constant force spring and a 0.16 cm (0.06 in.) thick black neoprene couplant 15. A received signal 16 may be amplified, as by an AET 204B instrument 17, using a total gain of 50 dB and a 0.125-MHz filter 18. An amplified signal 19 may be then sent to a separate true RMS converter 20 with a 25 millisecond response time, after which it may be digitized and stored as a digitized signal 21 in an IBM PC/AT 22 at a rate of 100 samples/second. When only a one channel acoustic emission system is available, the calibration cut and actual test cut may be done separately. This does not appear to be a severe limitation, since the amplitudes between successive cuts do not change significantly. This is due, in part, to the fact that a carbide cutter 10 was used, as well as the fact that the rate of chip formation does not change between successive cuts.

Figure 4:
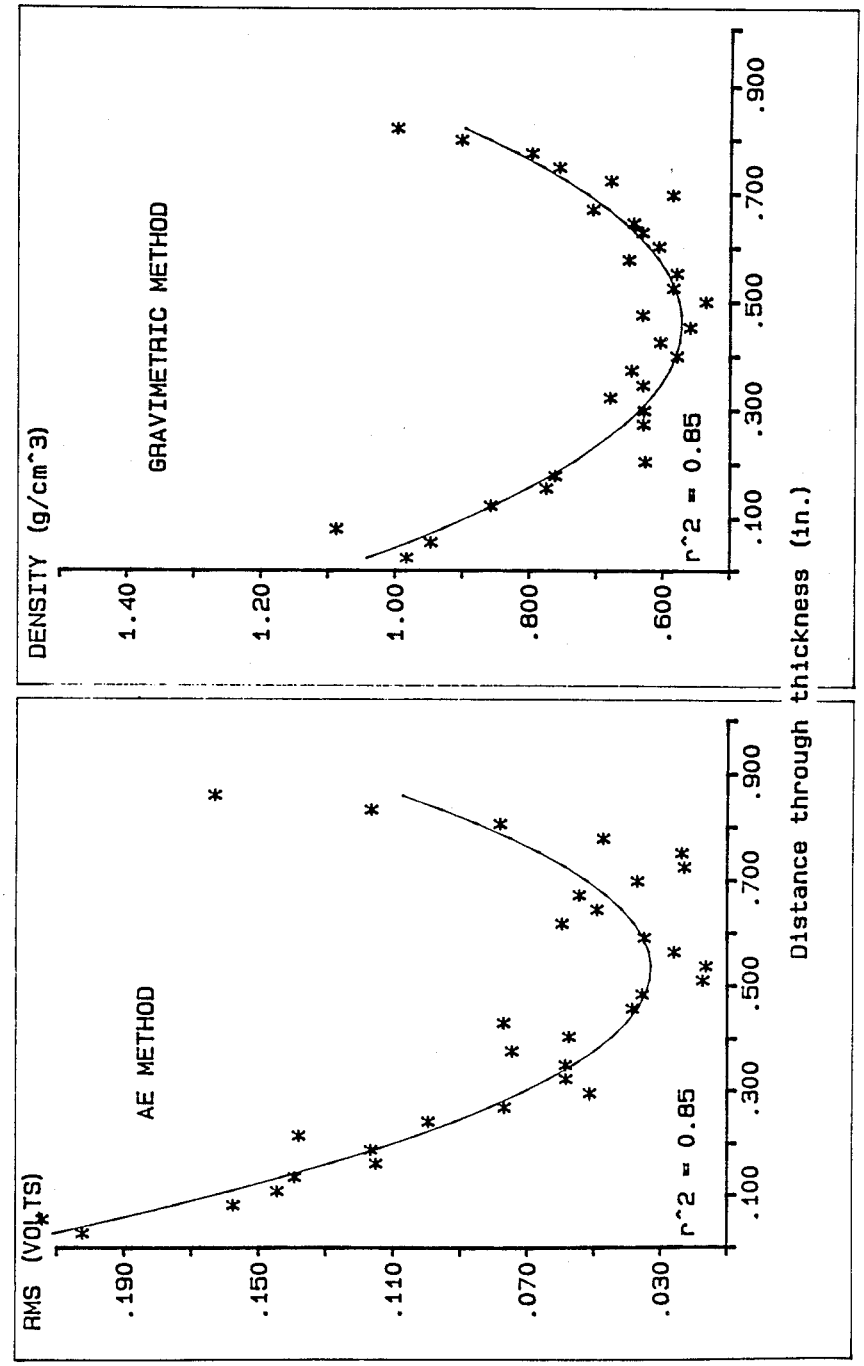
FIG. 4 is a graph of the RMS voltage plotted against thickness obtained from the apparatus and material of FIG. 2 compared with a similar graph obtained from the gravimetric method both for high density 3-layer particle board.
Figure 5:
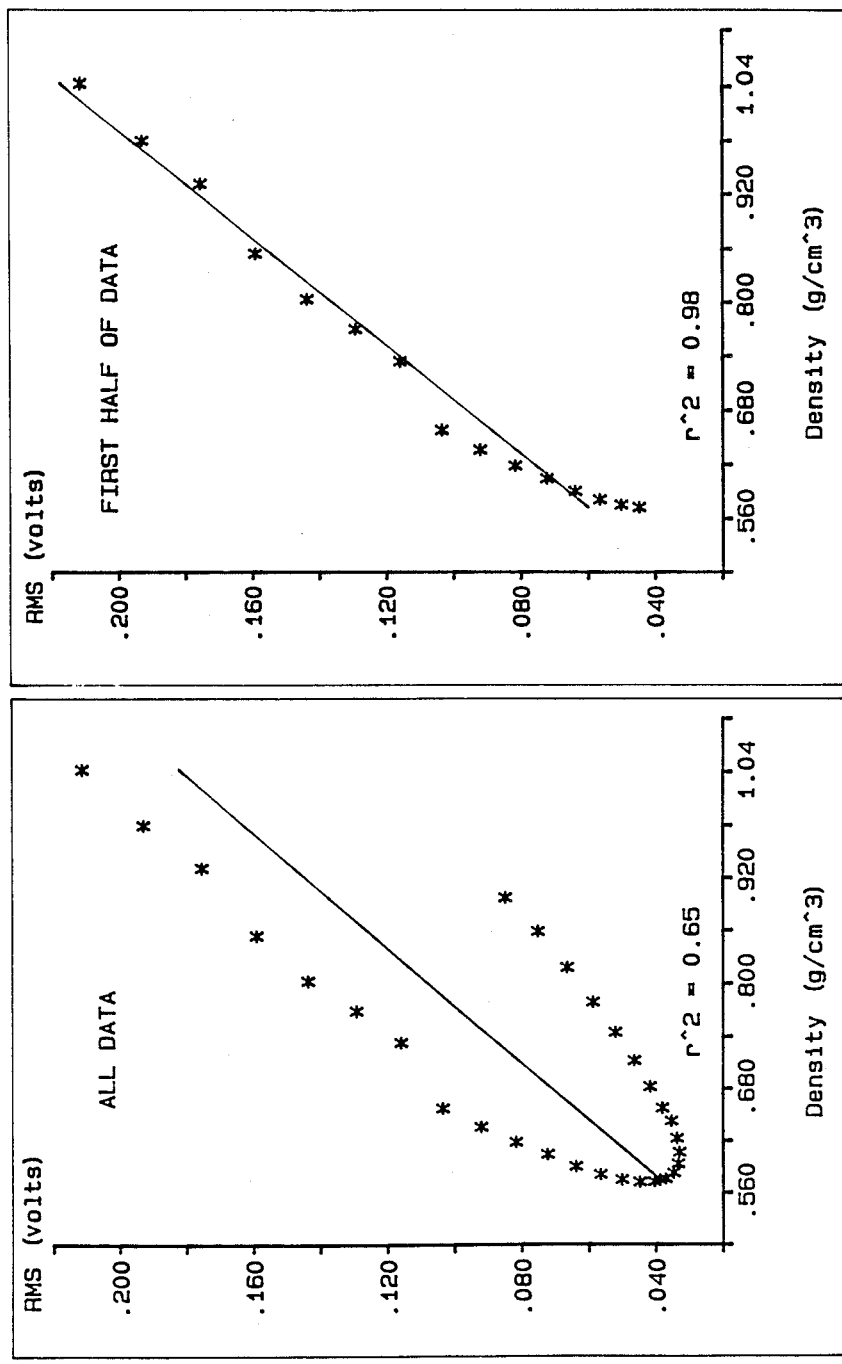
FIG. 5 is a graph showing the effect of material thickness when plotting RMS voltage against gravimetric density.

FIG. 4 shows a plot of the RMS data and the corresponding gravimetric density data for a high density industrial (3 layer) particle board 30. A second order polynomial is fitted to the data. The RMS data is not as smooth This roughness may be minimized by using a higher arbor speed (i.e., router) and/or a small diameter cutting tool 10.

One disadvantage of this method which should be taken into account is that the distance between the transducer 14 and the cutting tool 10 changes constantly during testing. Since wood and wood composites are so attenuative, this can have a significant effect on the RMS signal.

In FIG. 4 the transducer 14 was placed on the front face of the specimen 13, and data collected as the blade 10 moved completely across the thickness of the specimen 13. As can be seen from the plot of RMS versus gravimetrically determined density, there may be a significant thickness effect. If only the first half of the data is used the linear correlation between RMS and density improves dramatically. Subsequent experiments have been conducted with the transducer placed on the back face of the specimen. The thickness effect is still obvious but is reversed in nature.

By using only the second half of the data (from the midpoint of the specimen to the face where the transducer 14 was mounted) an excellent linear relationship between RMS and gravimetric density has been observed Any attempts that have been made to average the entire data set for both front and back face mounted transducer have met with only limited success. The loop in the curve of RMS versus density is less pronounced but is still evident. This was also reflected in the coefficient of determination ($r^2$) of 0.88 for the combined data. This could be improved upon by taking the front and back face data simultaneously on a two channel AE system. This would reduce the experimental error caused in the experiment by doing two separate cuts and remounting the transducer 44 between each cut.

Test results from the proposed density measurement techniques have shown the method to be extremely repeatable and accurate for use with composite wood materials. Whether specific densities or relative profiles were required, this method offered results quickly and safely with a relatively small amount of instrumentation, compared to the radiation methods.

Such a test still yields an accurate prediction of density. It also has the additional advantage of being essentially a non-destructive technique. This gives industry the option of using it either as a quick off-line quality control method or an on-line continuous process monitoring system.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A method for determining vertical density profiles in wood composites, comprising
   rotating a fly cutter across the edge of a wood composite panel to produce acoustic emissions that themselves produce an RMS voltage,
   while recording the changes in RMS voltage so produced 2. The method of claim 1 wherein the recording step includes
   detection of the acoustic emission,
   transforming the detected signal into electrical signals, and
   amplifying and transmitting the electrical signal to a suitable detecting transducer.

3. The method of claim 2 wherein said transducer chosen from the group consisting of oscilloscopes, counters, RMS voltmeters, recorders and spectrum analyzers.

4. The method of claim 2 wherein the transducer is a piezoelectric ceramic element.

5. The method of claim 4 where the piezoelectric ceramic element is lead zirconate titanate.

6. The method of claim 2 comprising statistical interpretation of the electrical signals.

7. The method of claim 2 wherein the voltage V of the AE signal is expressed by the equation $$V = V_o e^{-\beta t} \cos 2\pi f t$$

where
$V_o$ = the threshold voltage
$V$ = the initial output voltage of the transducer
$\beta$ = the damping factor
$f$ = the linear frequency
$t$ = time in seconds.

8. The method of claim 7 wherein the RMS voltage or value of $$V = \left[ \frac{1}{\Delta T} \int_o^{\Delta T} V^2(t)dt \right]^{\frac{1}{2}}$$

where
$V(t)$ = the function of the signal with respect to time.
$\Delta T$ = the time period.

9. Apparatus for determining vertical density profiles in wood composites, comprising
   a fly cutter,
   means for rotating said fly cutter across the edge of a wood composite panel to produce acoustic emissions that themselves produce an RMS voltage, and
   recording means for recording the changes in RMS voltage so produced.

10. The apparatus of claim 9 said recording mean detection means for detecting the acoustic
    transducing means for transforming the detected signal into electrical signals, and
    an amplifier for amplifying said electrical signal,
    a signal detecting transducer, and
    transmitting means for sending said electrical signal to said detecting transducer.

11. The apparatus of claim 10 wherein the transducer is a piezoelectric ceramic element.

12. The apparatus of claim 11 wherein the piezoelectric ceramic element is lead zirconate titanate.

* * * * *